United States Patent
Christensen et al.

(10) Patent No.: US 7,150,818 B2
(45) Date of Patent: Dec. 19, 2006

(54) PROCESS FOR ELECTROCHEMICAL DEPOSITION OF TANTALUM AND AN ARTICLE HAVING A SURFACE MODIFICATION

(75) Inventors: John Christensen, Nordborg (DK); Erik Christensen, Hellerup (DK)

(73) Assignee: Danfoss A/S, Nordborg (DK)

( * ) Notice: Subject to any disclaimer, the term of this patent is extended or adjusted under 35 U.S.C. 154(b) by 410 days.

(21) Appl. No.: 10/469,017

(22) PCT Filed: Feb. 26, 2002

(86) PCT No.: PCT/DK02/00127
§ 371 (c)(1),
(2), (4) Date: Aug. 26, 2003

(87) PCT Pub. No.: WO02/068729
PCT Pub. Date: Sep. 6, 2002

(65) Prior Publication Data
US 2005/0258047 A1      Nov. 24, 2005

(30) Foreign Application Priority Data
Feb. 26, 2001  (DK) .............................. 2001 00314

(51) Int. Cl.
*C25D 3/66* (2006.01)
*C25D 5/18* (2006.01)
(52) U.S. Cl. ..................................... 205/103; 205/230
(58) Field of Classification Search ................... None
See application file for complete search history.

(56) References Cited

U.S. PATENT DOCUMENTS

| 3,878,079 | A | 4/1975 | Schauer |
| 5,282,861 | A | 2/1994 | Kaplan |
| 6,203,684 | B1 * | 3/2001 | Taylor et al. ............... 205/103 |

FOREIGN PATENT DOCUMENTS

| EP | 0 578 605 A1 | 1/1994 |
| EP | 0 997 116 A2 | 5/2000 |
| JP | 6-57479 | 3/1994 |
| WO | WO 98/46809 | 10/1998 |

OTHER PUBLICATIONS

Bockis, et al, "9.2. The Transient Behavior of Interfaces", from Modern Electrochemistry, vol. 2, pub. by Plenum Press, Apr. 1973, pp. 1017-1036.*
Lee S. L. et al.: "Analysis of Magnetron-sputtered Tantalum Coatings Versus Electrochemically Deposited Tantalum from Molten Salt", Surface and Coatings Technology 120-121, U.S. Army Armament Research Development and Engineering Center, Benet Laboratories, Watercliet, NY, 1999 pp. 44-52.

* cited by examiner

*Primary Examiner*—Harry D Wilkins, III
(74) *Attorney, Agent, or Firm*—McCormick, Paulding & Huber LLP

(57) ABSTRACT

A process for electrochemical deposition of tantalum on an article in an inert, non-oxidizing atmosphere, or under vacuum, in a molten electrolyte containing tantalum ions, comprising the steps of: immersing the article into the molten electrolyte heated to a working temperature, passing an electric current through the electrolyte to thereby deposit a tantalum coating on the article, wherein the process of tantalum deposition at least in an initial phase deposits pure α-tantalum.

10 Claims, 7 Drawing Sheets

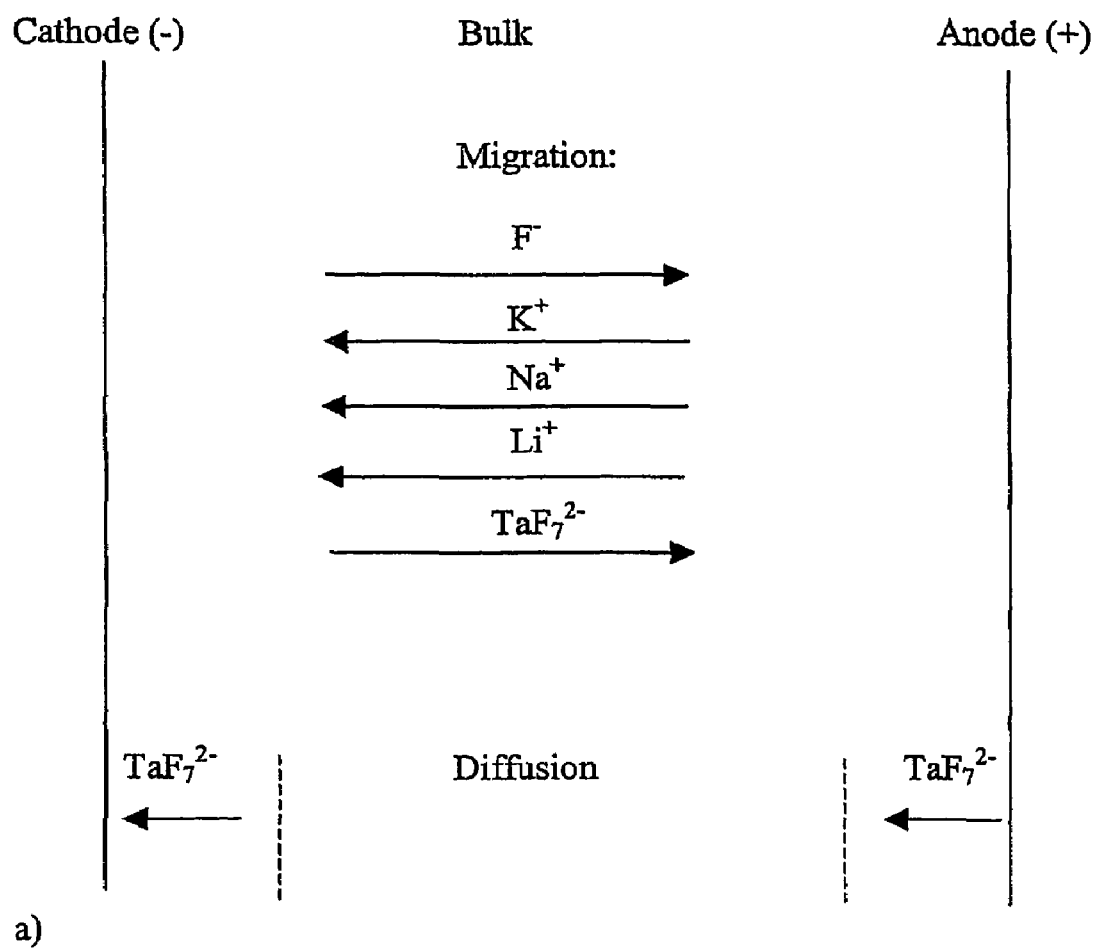
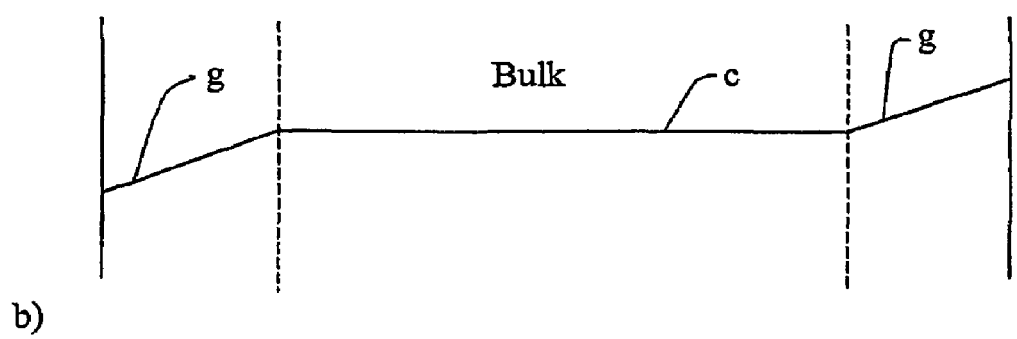
Fig. 1

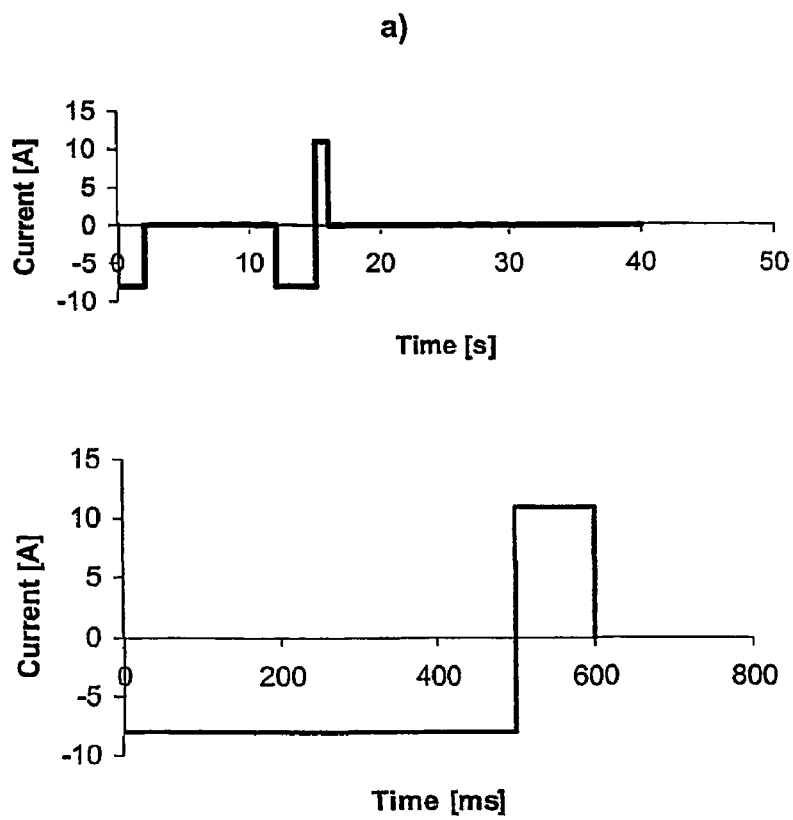
Fig. 8 a and b
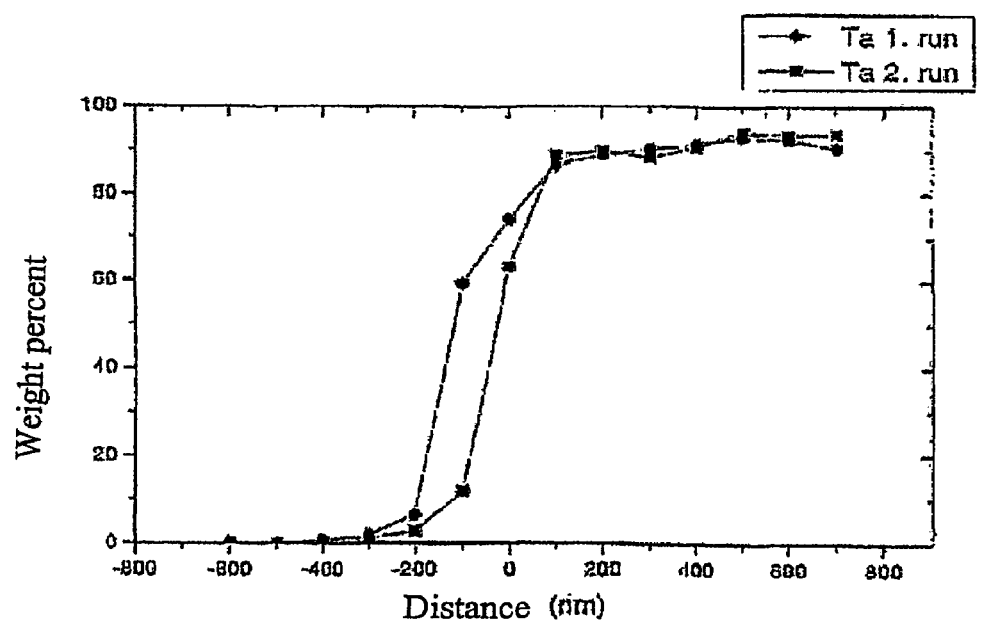
Fig. 9

PROCESS FOR ELECTROCHEMICAL DEPOSITION OF TANTALUM AND AN ARTICLE HAVING A SURFACE MODIFICATION

CROSS-REFERENCE TO RELATED APPLICATIONS

This application is entitled to the benefit of and incorporates by reference essential subject matter disclosed in International Application No. PCT/DK02/00127 filed on Feb. 26, 2002 and Danish Patent Application No. PA 2001 00314 filed on Feb. 26, 2001.

FIELD OF THE INVENTION

The present invention relates to a process for electrochemical deposition of tantalum on an article in an inert, non-oxidizing atmosphere, or under vacuum, in a molten electrolyte containing tantalum ions, comprising the steps of:

immersing the article into the molten electrolyte heated to a working temperature, passing an electric current through the electrolyte to thereby deposit a tantalum coating on the article, using the process of tantalum deposition to at least in an initial phase deposit pure α-tantalum.

Further the invention relates to an article, such as an implant, provided with a surface modification of tantalum by the above process.

BACKGROUND OF THE INVENTION

The last fifty years a lot of effort has been made to provide a way to provide articles of e.g. steel with a surface layer of corrosion resistant material, such as tantalum. Tantalum possesses corrosion resistance even at high temperatures, so this material is advantageous in many fields where products are subject to corrosion. Further tantalum is a biocompatible and tissue-friendly material, so it is well suited for application in the medical field, such as for implants.

Known techniques for depositing refractory metals, such as tantalum, on an article, involve electroplating in an electrolyte comprising a mixture of fused salts, the mixture including a salt or salts of the refractory metal with which the article is to be plated. WO 98/46809 discloses a method for electroplating with a refractory metal. According to this method a molten electrolyte is used, said electrolyte consisting of refractory and alkali metal fluorides and a melt of sodium, potassium and caesium chlorides, and electrical current is passed through the electrolyte in alternating, repeating cycles. Methods for electroplating using mixed chloride-fluoride melts have, however, a tendency to result in porous coatings and coatings having a low adherence. Further caesium is very expensive, so therefore this method is not suited for industrial application.

EP 0 578 605 by the applicant in the present application discloses a fused-salt bath and a process for electrolytic surface coating. The bath comprises an alkali fluoride melt containing oxide ions and ions of the metal to be deposited.

SUMMARY OF THE INVENTION

An object of the invention is to provide a process for electrochemical deposition of tantalum depositing smooth surface modifications that do not crack or peel off.

The process according to the invention is characterized in applying the electrical current in a first type of cycles in a nucleation phase, said first type of cycles comprising at least one cathodic period, followed by at least one anodic period, and a pause.

Tantalum is an allotropic material having two different kinds of lattice structure: α-tantalum and β-tantalum. It is found that α-tantalum, having a body-centered cubic lattice, is more ductile than β-tantalum, having a tetragonal lattice. β-tantalum is relatively hard (2000 Knoop versus 300–400 for α-tantalum) and there is a risk that a layer of β-tantalum may crack and/or peel off, either during the process or in use later. A visual inspection of the surface reveals whether the tantalum deposited is α-tantalum or β-tantalum, as α-tantalum is blue-grey, while β-tantalum is lighter in colour and greyish. As mentioned α-tantalum is ductile, and this means that a deposition of α-tantalum on a surface of a base material can follow any normal movement of the base material, e.g. because of difference in thermal expansion of tantalum and the base material. By initially depositing a pure structure of α-tantalum onto the surface of the article there is obtained a coherent ductile surface modification onto the base material resulting in minimum risk of cracks and/or peeling, and therefore the corrosion resistance and biocompatibility for an article modified with α-tantalum is high, even if the article is used in heavy duty.

An electrolyte based on a mixture of chlorides and fluorides can be used, but using a electrolyte based on a melt of fluorides and containing substantially no chlorides and having a ratio of refractory metal to oxide content higher than 3:1 is found to be advantageous, as the resulting deposition to a higher degree is smooth and non-porous, and the α-tantalum more easily obtained.

Although direct current can be used, it is found to be advantageous to apply the electrical current in a first type of cycles in a nucleation phase, said first type of cycles comprising at least one cathodic period, followed by at least one anodic period, and a pause. The use of alternating cathodic and anodic periods reduces the risk of dendrite formation and growth, and further reduces the risk of uneven distribution of metal ions and uneven current density associated with articles of complex geometry. It is found that a pause after the anodic period will stimulate the formation of α-tantalum, presumably because the pause leaves time for the species to convert and nucleate as α-tantalum.

By applying the current during the nucleation phase with a current density above the current density of deposition of β-tantalum, but below the limiting current density, it is found that pure α-tantalum can be achieved.

In electrolysis, the charge on the electrode surface is always balanced by attracting ions of opposite charge from bulk solution to the immediate vicinity of the surface. This means that in the electrode-electrolyte interface two layers of opposite electrical charge exists: the electrical double layer. The double layer is analogue to an electrical capacitor, and it takes a certain time to charge and discharge the double layer. By applying current pulses having duration longer than a charge/discharge period of a double layer, it is found that pure α-tantalum can be achieved.

The duration of the pause is chosen to be longer than the duration of the cathodic and anodic period of the cycle, preferably 2–8 times longer, in particular 4 times longer. The duration of the pause is a compromise between formation of α-tantalum and the overall duration of the nucleation phase.

Another object of the present invention is to provide an article having improved corrosion resistance.

To achieve this the surface modification is non-porous and at least comprises an interface layer of α-tantalum. α-tantalum is especially advantageous as interface layer, as it has high ductility and hence this layer will counteract formation of cracks and peeling of the surface modification, and further it will seal off the surface.

The surface modification may have any suitable thickness, but it is recommended that the surface modification has a thickness of about 2–14 μm, preferably more than 5 μm and less than 12 μm, and in particular 8–10 μm. A thickness of the outer zone of 2 μm may be sufficient by simple geometrical forms of the base body, but with holes and edges, the modification will result in a thinner outer zone and thus a risk of a porous surface. A thickness of the outer zone of more than 14 μm will entail an increase of the process time and more considerable material expenses, and this will thus be unfavourable for economic reasons. It has turned out that a thickness of the outer zone of 8–10 μm makes a reasonable compromise between certainty of a sufficiently thick outer zone over the entire base body and economy.

BRIEF DESCRIPTION OF THE DRAWINGS

In the following the invention will be further illustrated with reference to embodiments and the drawing, where:

FIG. 1 is a schematic representation of charge transport and concentration profile through an electrolytic cell, FIG. 8 is graphs of current pulses, FIG. 9 shows a graph indicating the quantity of tantalum, which has penetrated a base body of a Co—Cr—Mo alloy.

DETAILED DESCRIPTION OF THE PREFERRED EMBODIMENTS

Figure 2:
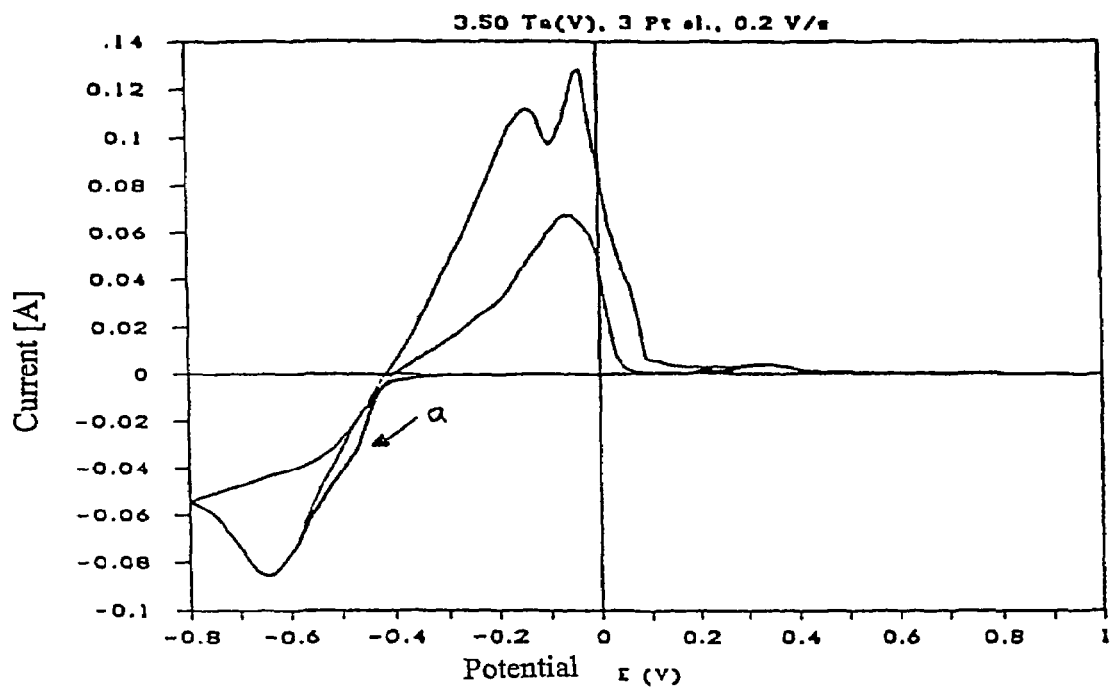
FIG. 2 is two voltammograms of a process.

In the following examples, the melt used is a mixture of Lithium Fluorides (LiF), Natrium Fluorides (NaF) and Kalium Fluorides (KF). As source of metal ions can be used an anode made of tantalum, however in the example a platinum anode is used and as source of tantalum ions $K_2TaF_7$ is used, e.g. in the form of pellets, and tantalum is present in dissolved form as $TaF_7^{2-}$ ions in the melt. The tantalum dissociate into ions so tantalum is present in oxidation number five, meaning that the tantalum has lost five electrons, and at reduction is reduced to tantalum metal in a five-electron process, i.e. the reduction takes place in one step from tantalum in oxidation number five (Ta(V)) to oxidation number 0 (Ta(0)), i.e. metal. At the cathode the deposition takes place as a process of the form

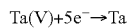

while at the anode the reverse process takes place

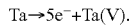

In FIG. 1a can be seen a schematic representation of charge transport and in FIG. 1b can be seen a schematic representation of the concentration profile through an electrolytic cell. The electrolyte is completely dissociated in positively and negatively charged ions $K^+$, $Na^+$, $Li^+$, $F^-$ and $TaF_7^{2-}$. By applying an electrical field these ions move by migration, i.e. an electrostatic phenomenon. Migration leads to an increase in concentration of $TaF_7^{2-}$ in the anode vicinity and a corresponding decrease in concentration near the cathode, i.e. the article to be provided with a deposition of tantalum. The electrode vicinities are called diffusion layers or "boundary layers" (shown with dashed lines, and the area between the two vicinities is called bulk. It is normally assumed that no substantial change of concentration takes place in the bulk, as the constant concentration "c" of the reactant ($TaF_7^{2-}$) is maintained by a combination of migration, diffusion and convection. In the anode vicinity a concentration increase takes place because of dissolution of the anode and a decrease in the cathode vicinity because of metal deposition, and in these diffusion layers there is a concentration gradient "g". The concentration gradient "g" gives rise to diffusion, which is a physical phenomenon. In the electrolysis the following elements form part of an electrochemical metal deposition process:

transport of charge and matter through the bulk, transport of charge and matter through the diffusion layer, charge transfer process (reduction of metal ions to metal in the electrode region), crystallisation of reduced metal atoms leading to the development of surface layer.

One or more of these elements can control deposition of metal:

by kinetic control or activation control, the process is controlled by the velocity of charge transfer, so in this case the problem is to make the metal deposit on the cathode, while by diffusion control, the process is controlled by the velocity of charge transport, so in this case the problem is to provide a sufficient amount of metal ions near the surface of the cathode.

The kind of control in any given example is controlled by the current density in relation to the limiting current density. The current density is the ratio of the current to the area of the electrode, and the limiting current density is the current density, where the surface concentration of reactant (i.e. in this case $TaF_7^{2-}$) falls to zero, i.e. applying a current density greater than the limiting current density results in a depletion of the electrode vicinity with regard to reactants after a certain time, as the electron transfer (or deposition) is faster than the inflow of reactant into the diffusion layer. After depletion of the cathode vicinity, the reduction of $TaF_7^{2-}$ is completely controlled by diffusion, so the rate of transport of $TaF_7^{2-}$ to near the surface of the cathode is conclusive for the rate of deposition of $TaF_7^{2-}$.

As mentioned above, tantalum is an allotropic material, so for tantalum there exists two kinds of lattice structure. Body-centered cubic lattice denoted α-tantalum and tetragonal, metastable lattice denoted β-tantalum. It is found that α-tantalum, having a body-centered cubic lattice, is more ductile than β-tantalum, having a tetragonal lattice. β-tantalum is hard and there is a risk that a layer of β-tantalum may crack and/or peel off, either during the process or in use later. By most processes, however, there is a tendency that deposition of the unfavourable β-tantalum will take place—this is true for Physical Vapour Deposition (PVD) processes and fused salt processes.

For the tantalum deposition process cyclic voltammograms can be seen in FIG. 2. Voltammograms are achieved by linear variation of the overpotential and plotting the current in response hereto. The variation is fast, so the process is not in a stationary condition. By applying the overpotential (i.e. a deviation of the potential from the equilibrium potential) in a cycle of cathodic and anodic direction, information of the process or the processes can be achieved. In FIG. 2 two voltammograms are shown, one being obtained in the potential interval [−600 mV;+1000 mV] and the other in the interval [−800 mV;+1000 mV]. In the first one a cathodic shoulder can be seen at −475 mV (shown with an "a") and in the second one, a cathodic peak can be seen at −620 mV. By X-Ray Diffraction, it can be seen that the metal deposited at the shoulder at −475 mV is β-tantalum, and the metal deposited at the peak at −620 mV is α-tantalum.

Figure 3:
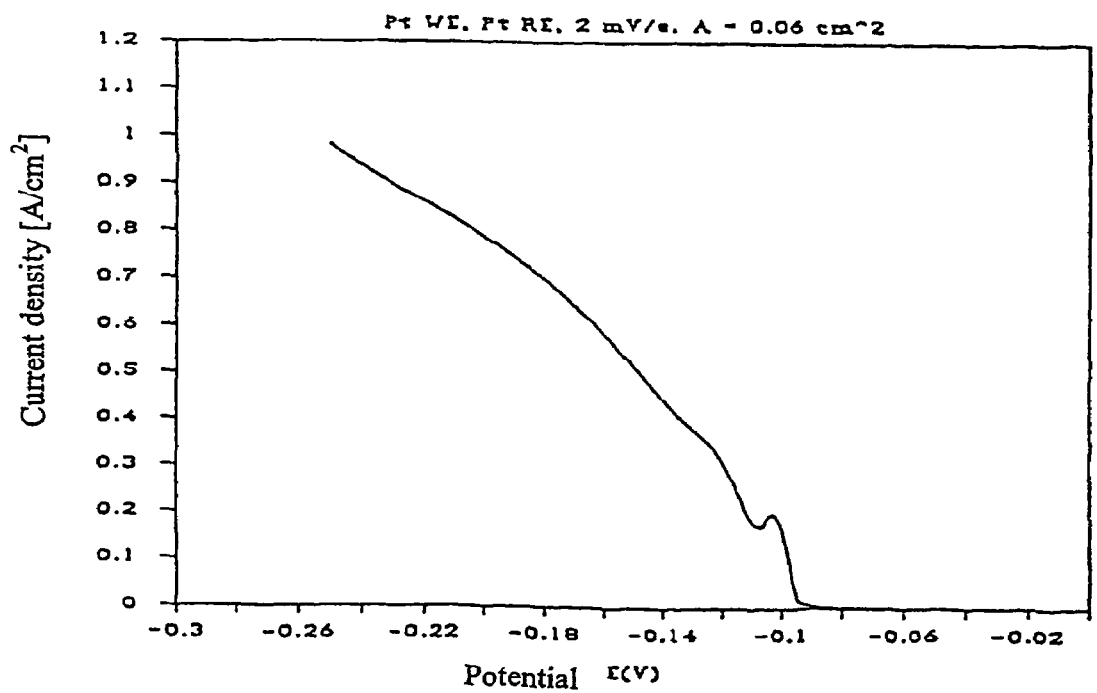
FIG. 3 is a stationary polarisation curve.

Further information can be achieved by stationary polarisation curves achieved by an increase of the overpotential so slow that stationary condition is maintained. Stationary polarisation curves provide information on the number of processes taking place and the limiting current densities for the processes. The stationary polarisation curves in FIG. 3 are obtained at an increase of the overpotential of 2 mV/s, so the stationary condition is maintained, and it can be seen that two processes take place. One process is seen to begin at −90 mV and another one at −110 mV, and by X-Ray Diffraction it can be found that these processes are deposition of β- and α-tantalum, respectively. Further increase of the current density results in an approximately linear curve, still with deposition of α-tantalum. At approximately −800 mA/cm$^2$, however, the slope of the curve is minimum, indicating that the limiting current density has been reached. That the slope of the curve is not horizontal at the limiting current density is due to the fact that the area of the electrode increases because of the metal deposition.

Figure 4:
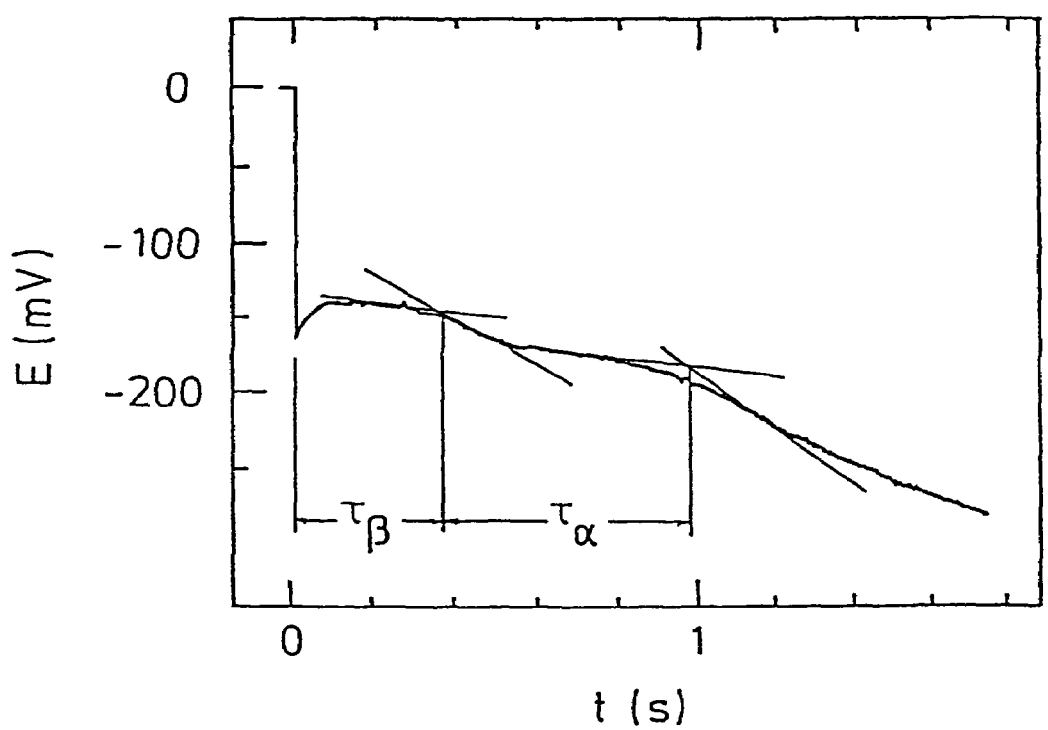
FIG. 4 is a chronopotentiogram.
Figure 5:
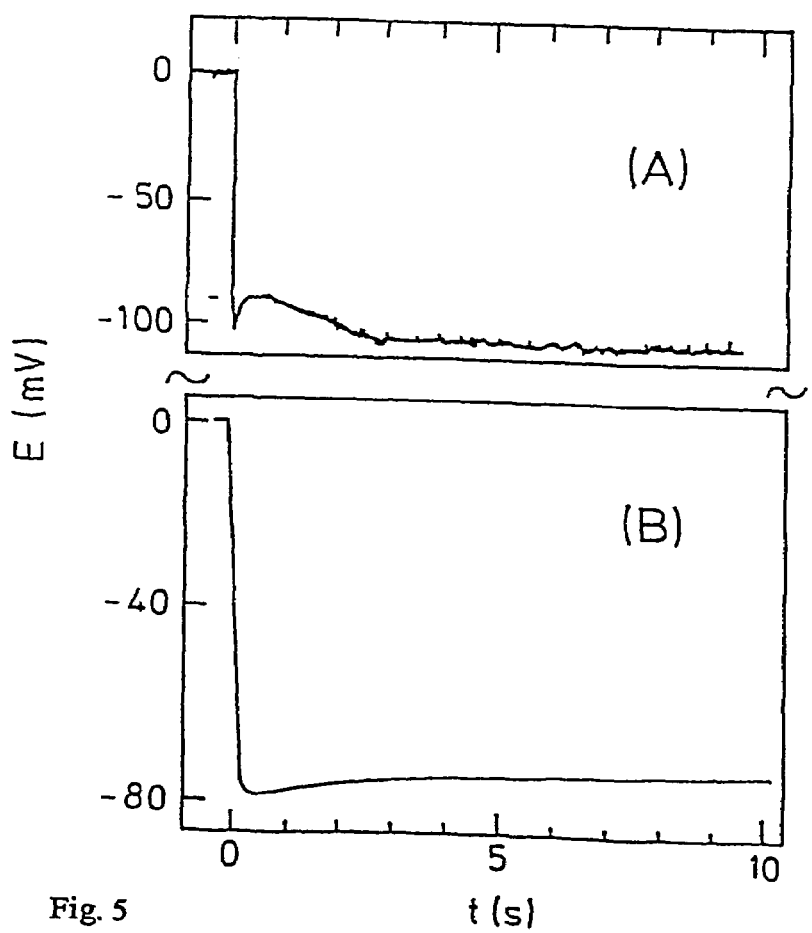
FIG. 5 is a chronopotentiogram.

FIGS. 4 and 5 are chronopotentiograms, where a current step is applied to the electrolytic cell. In FIG. 4 a current density of −1200 mA/cm$^2$ is applied, i.e. a current density greater than the limiting current density, and it can be seen there are two plateaus, one at −140 mV and one at −180 mV, indicating the two processes take place. It can be found that which are the overpotentials for deposition of β- and α-tantalum, respectively. It can be seen that at the applied current density diffusion control for deposition of β-tantalum takes place after 360 ms, while diffusion control for deposition of α-tantalum takes place after 1 s, as at these points there is an increase in potential showing that the limiting current density of the process referred to is reached. The chronopotentiogram according to FIG. 5 is obtained at a current density of −300 mA/cm$^2$, i.e. a current density much lower than the limiting current density of −800 mA/cm$^2$ as mentioned above. In this figure a plateau at −90 mV can be seen. After 800 ms this process is diffusion controlled, and after 2.7 s a potential of −110 mV is reached.

By comparison of FIG. 3 and FIG. 5, it can be seen that the process of deposition of β-tantalum takes places at diffusion control, while the α-tantalum deposition process is not diffusion controlled.

Figure 6:
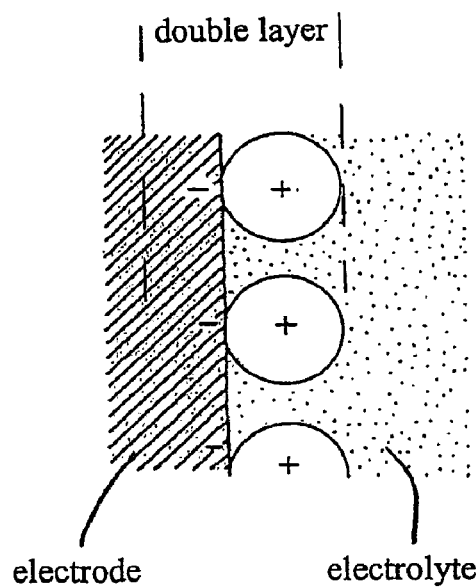
FIG. 6 is a schematic view of the electrode vicinity.
Figure 7:
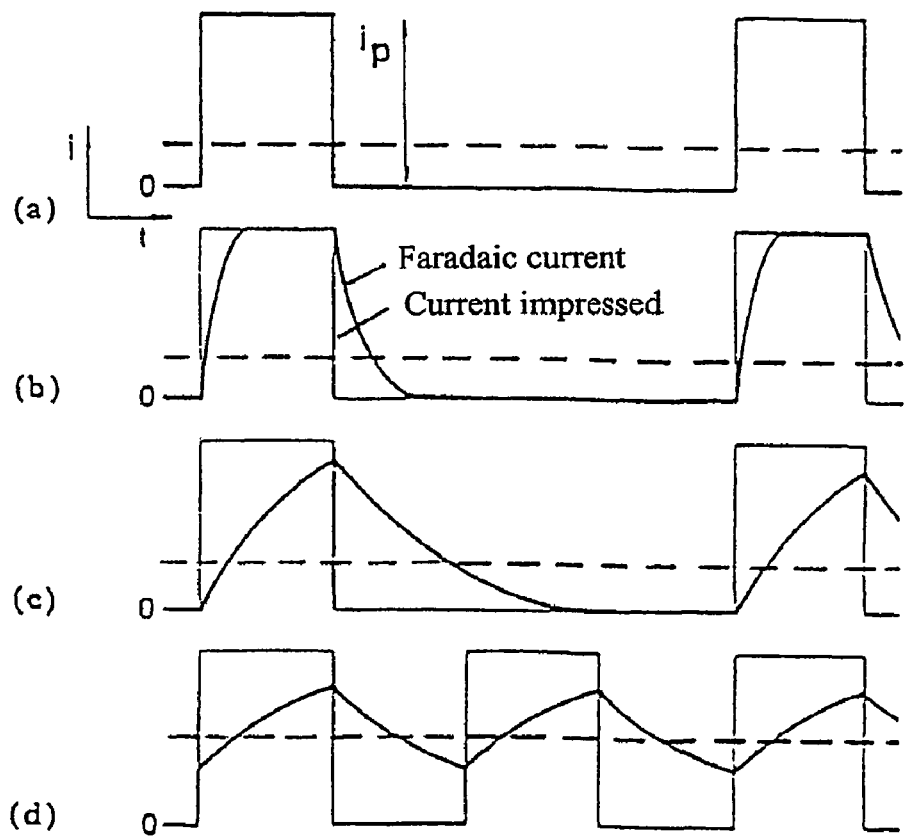
FIG. 7 is graphs of current pulses.

FIG. 6 is a schematic view of the electrode vicinity. On the side of the electrolyte, the partial charge is shielded in that in the near boundary (vicinity) of the electrode an excess of ions of opposite charge is accumulated. In the electrode-electrolyte interface two layers of opposite electrical charge exists: the electrical double layer. The double layer is analogue to an electrical capacitor, and it takes a certain time to charge/discharge the double layer. As can be seen in FIG. 7, the charge/discharge of the double layer cause the curves of the Faradaic current to smoothen. FIG. 7a is a representation of the current applied as a step, whereas FIG. 7b is a plot of the current impressed and the Faradaic current, i.e. the current available to the reduction process. As can be seen, the Faradaic current is not identical to the current impressed, as the charge and discharge of the double layer takes time. As mentioned the Faradaic current is the current available for the reduction process, so this means that pulse effect is reduced. Regarding the lower limit of the pulse duration, it applies that the pulse duration must be longer than the charge/discharge duration of the double layer. In FIG. 7c is shown a situation, where the charging time is so long that the current impressed is not even achieved within the step period, and in FIG. 5d a situation is shown, where current steps are applied at a rate faster than the charge and discharge period of the double layer, so the steps are almost completely smoothened out.

The prerequisite for a cathodic metal deposition process to take place is that the metal ions are present in sufficient proximity of the cathode for electron transfer to take place. The prerequisite for deposition of metal ions on the cathode to take place evenly distributed is that the metal ions prior to the reduction process is correspondingly evenly distributed around the cathode. Further the even distribution must always be maintained during the electrolysis.

Formation of dendrites is caused by the phenomena that surface roughness (irregularities) is magnified during the deposition process because of increased current density right there compared to the rest of the cathode surface. Coatings without dendrites can be achieved by deposition under kinetic control.

A way to ensure sufficient amounts of metal ions near the electrodes and even distribution of metal ions is by agitation of the electrolyte or rotation of the cathode. Another way is to periodically changing the direction of the current, so that the article to be coated alternately is cathode and anode. By periodically changing direction of the electrolysis current, the electrode concerned will periodically operate as anode from where metal deposited again is dissociated into ions. Hereby the surface concentration, dependent on the pulse period and the current density, can be increased so much that it can exceed the bulk concentration, which increases the chance of avoiding depletion of the electrode vicinity. As can be understood, it is possible by pulsing the electrolyte current to influence the conditions of diffusion and electron transfer velocity towards kinetic control, and thereby influencing the deposition process positively regarding avoiding dendrite growth.

Unlike direct current electrolysis, where the electrolysis current density must be considerably smaller than the limiting current density, pulsed electrolysis provides greater choice of electrolysis current density, and thereby greater possibility to optimise the deposition process, while meeting the requirement of kinetic control. By pulsing the electrolysis current, by periodical current interruption, a double diffusion layer is established at the interface between bulk and electrode surface. The reason for this is that only the concentration conditions in the nearest vicinity of the electrode is changed by fast pulsing (i.e. by pulsing faster than the time needed for establishing the stationary diffusion layer), while the concentration profile from this vicinity outwards is identical to the stationary profile by the corresponding average current density. During the pulse pauses ions are constantly supplied to the nearest cathode vicinity, without by deposition a removing takes place. Thereby a concentration profile varying in time is created, this concentration profile varying with the pulse frequency; a pulsating diffusion layer being thinner than the stationary diffusion layer. The increased surface vicinity concentration by the end of a pulse pause gives the opportunity of a corresponding increase of pulse current density, without the surface concentration become zero.

An important detection is that β-tantalum will not deposit on α-tantalum, i.e. in a nucleation phase it is important to ensure the right parameters to avoid deposition of β-tantalum, but after a covering surface modification of α-tantalum is formed, there is no risk of deposition of β-tantalum, so focus can be on parameters to avoid formation and growth of dendrites.

In an example, four cylinders made of vitallium were treated by the process, the area of the cylinders being 178 cm$^2$. The concentration of the electrolyte was 3.5 mole % tantalum (oxidation number 5), and the working temperature was 700° C. For application of current pulses a potentiostat/galvanostat was used (Solartron 1286 Electrochemical Interface; Schlumberger Technologies). A program for treatment of the cylinders involve an initial 20 minute warm up phase, where the cylinders are placed in the electrolyte, but no current is applied, a nucleation phase taking 20 minutes and applying current in a first series of special cycles, and a phase of building up of the surface modification taking 38.30 minutes and applying current in a second series of special cycles.

The nucleation phase involves 30 cycles of 40 s each. As can be seen in FIG. 8(a) each cycle comprises a first cathodic period of duration of 2 s, a 10 s pause, a second 3 s cathodic period, a 1 s anodic period, and a pause of 24 s. In the cathodic period the current applied is 8 A, and in the anodic period 11 A.

The second series of special cycles for building up of the surface modification involves 3850 cycles of 600 ms each. As can be seen in FIG. 8(b), each cycle comprise a cathodic period of 500 ms and a anodic period of 100 ms, the current applied being 8 A and 11 A, respectively.

The current applied in the anodic period is chosen to be higher than the current applied in the cathodic period. This is because a higher current in the anodic period of the cycle will increase the polishing effect of the anodic period of the cycle, where metal is removed from the surface of the article, as the higher current will concentrate at irregularities of the surface, such as dendrites.

The duration of the application of current in the cathodic and anodic period of the cycles is chosen so that the ratio of the amount of electrical charge in the cathodic period to the amount of electrical charge in the anodic period is 4:1. This ratio seems to provide an appropriate compromise between speed of the process and quality of the surface modification. Higher ratios will of course result in rapid development of the surface modification, but with an increasing risk of dendrite formation and pinholes.

The process alloys tantalum into the surface and this means that a metal body in a hardened form is exposed to a process which alloys tantalum into the surface of the base body, and that the surface thus has an alloy zone, the tantalum diffusing up to some micrometers into the body. The application of the tantalum continues until it forms an outer zone with a uniform, diffusion-tight surface of essentially pure tantalum. The outer zone proceeds gradually to the alloy zone, which is structurally anchored completely in the base body. The outer zone has a higher ductility than the metallic base body, i.e. that the outer zone has higher deformation ability than the base body such that the outer zone can be extended longer than the base body.

When producing metal articles, micro and macro cracks are formed on the surface of the metallic base body, and these cracks cannot be completely removed by subsequent treatment, even by polishing with e.g. diamond paste. Furthermore, the surface of the base body will be provided with grain boundaries, and both grain boundaries and cracks cause notch effect during fatigue, thus facilitating the initiation of crack growth from the surface of the base body, which may lead to fractures, and further the cracks may be subject to corrosion. As the outer zone is uniform and impervious, all cracks and grain boundaries on the surface of the base body is efficiently sealed. The implant surface is free from notch effect, the surface being without grain boundaries, cracks or anything from where a crack may initiate, which entails that the fatigue strength and corrosion resistance is substantially increased.

These advantages apply to all metal articles. Regarding implants there is a further advantage that a diffusion-tight outer zone of a biocompatible material is provided. Further the fatigue strength is of crucial importance to the durability of implants as most implants are exposed to repeated load. A hip implant at ordinary walk will thus be affected about once per second, which means that for a person being out of bed for about 5 hours a day, the total number of loads in a year will be more than 6.5 million. Further, the higher ductility of the outer zone in relation to the base body means that this zone follows the movements of the base body and does not peel off.

An impervious surface without micro porosities is advantageous as bacteria have more difficulties in adhering to an impervious surface, and there is thus less risk of introducing bacteria when inserting the implant. This means that the healing process is not impeded by bacteria and the risk of complications is minimized.

According to a preferred embodiment, the metallic base body is a Co—Cr—Mo alloy which has proved to obtain a particularly high increase of fatigue strength by surface modification.

In a preferred embodiment, the base body is modified by a fused salt process to a thickness of the outer zone of about 2–14 μm, preferably more than 5 μm and less than 12 μm, and in particular 8–10 μm. A thickness of the outer zone of 2 μm may be sufficient by simple geometrical forms of the base body, but with holes and edges, the modification will result in a thinner outer zone and thus a risk of a porous surface. A thickness of the outer zone of more than 14 μm will entail an increase of the process time and more considerable material expenses, and this will thus be unfavourable for economic reasons. It has turned out that a thickness of the outer zone of 8–10 μm makes a reasonable compromise between certainty of a sufficiently thick outer zone over the entire base body and economy.

Figure 10:
FIG. 10 shows an enlargement at 600× magnification in an electron microscope of a base body with surface modification.

A base body 1, shown in FIG. 10, is lowered into a bath of melted salt to be covered by a material. Not all metals can withstand being lowered in a salt melt as the melt is strongly reactive, and thus e.g. titanium will be dissolved in a moment (fluoride salt melt). As can be seen in FIG. 10, a uniform diffusion-tight outer zone 2 of tantalum can be obtained with a thickness of the outer zone 2 of about 8–10 μm, and a so-called smooth surface is obtained which is completely even and smooth without grain boundaries by this process at appropriate control of electric impulses. An even and smooth surface is advantageous as there is a minimum risk of bacteria on the surface when inserting the implant.

By the fused salt process, an alloy of the modification material is obtained in the surface of the base body 1, the modification material diffusing a little into the base body 1. This is seen from, among others, FIG. 9 showing a measurement of the content of tantalum at different distances from the surface of a base body produced from Co—Cr—Mo and surface modified by tantalum. In FIG. 9, a distance of zero represents the surface of the base body 1, negative values positions in the base body 1, whereas positive values represent positions in the outer zone 2. It can thus be seen that in a depth of 100 nm (0.1 µm), there is a weight percentage about 40 of tantalum. This indicates that even in a base body made from Co—Cr—Mo having a rather closed surface, an alloying of tantalum takes place in the base body 1 which assures a complete anchoring of the outer zone 2, and thus that the outer zone 2 does not peel off.

FIG. 10 shows a sectional view of a surface modified base body 1 produced from a Co—Cr—Mo alloy modified by tantalum by a fused salt process. The outer zone 2 on the base body 1 has in this embodiment a thickness of about 15 µm. It has turned out that the thickness of the outer zone 2 when modified by tantalum by the fused salt process does not need to be larger than about 10 µm, however, there is nothing to prevent much thicker outer zones 2, e.g. of 50 µm.

Figure 11:
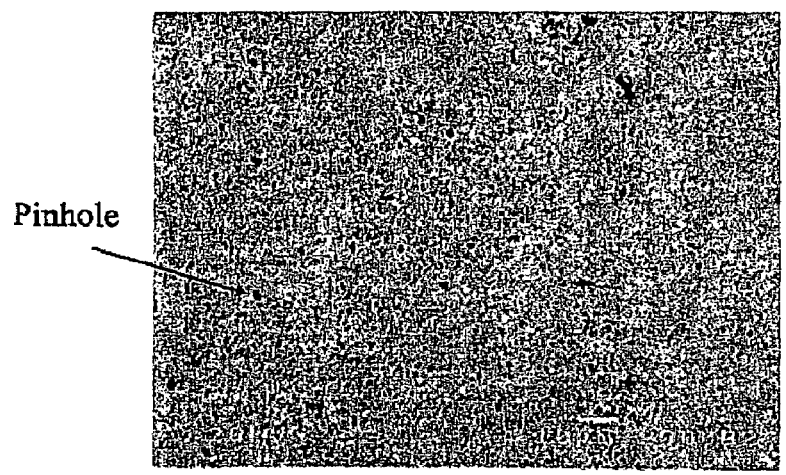
FIG. 11 is a surface modified surface with pin-holes.
Figure 12:
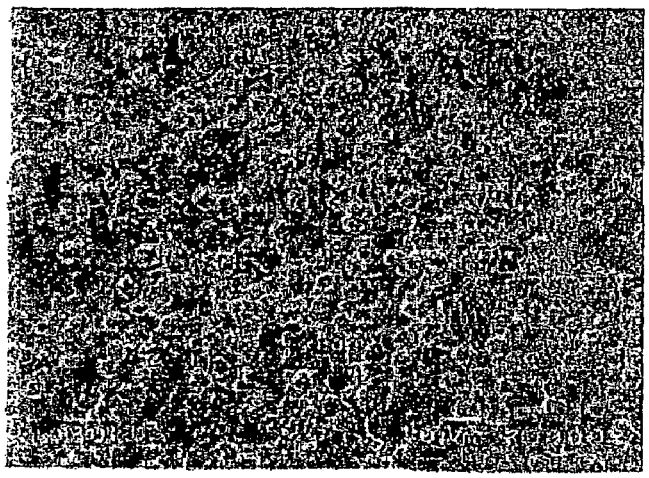
FIG. 12 is a surface modified surface without pin-holes.

As mentioned, it is essential that the outer zone 2 is uniform and diffusion-tight which may be difficult to obtain, especially as there is a risk that pin-holes will appear in the surface, this means that the outer zone 2 is provided with through-going holes. This is seen in FIG. 11 showing the surface of a surface modified base body. The black spots are such pin-holes. FIG. 12 shows a surface of a corresponding surface modified base body, and it can be seen that this surface is impervious and without pin-holes.

Figure 13:
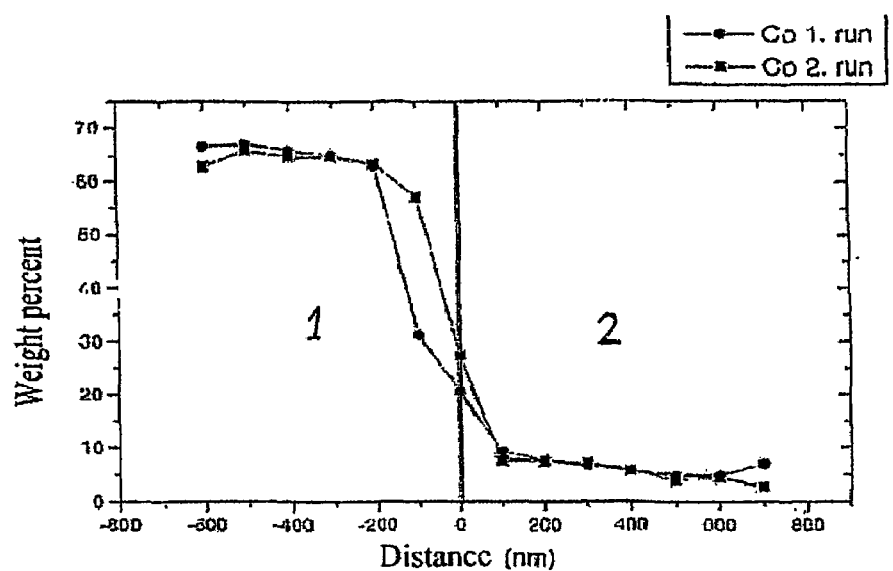
FIG. 13 shows a graph indicating the quantity of Co in the surface area of a tantalum modified base body produced from a Co—Cr—Mo alloy.

Since the implant according to the invention has a uniform and diffusion-tight outer zone, a diffusion barrier is thus provided to assure that unwanted substances in the base body, such as cobalt, do not diffuse out of the implant. As can be seen from FIG. 13 indicating the measured quantity of cobalt in the base body, alloy zone and outer zone of a tantalum modified base body made from a Co—Cr—Mo alloy, the measured quantity of cobalt reduces in the alloy zone from approx. 65% in the base body 1. Again a distance of zero represents the surface of the base body 1, negative values positions in the base body 1 and the alloy zone, whereas positive values represent positions in the outer zone 2. In this connection it should be remarked that the figure due to measuring technical limitations provides a somewhat misleading picture. In fact, cobalt is only present in the alloy zone where the quantity gradually approaches zero, whereas no cobalt is found in the outer zone.

Figure 14:
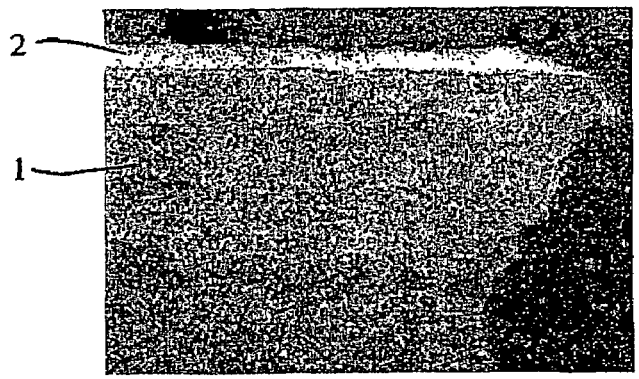
FIG. 14 shows a thin section perpendicular to a fracture zone of a surface modified base body.

FIG. 14 shows a thin section perpendicular to a fracture on a corresponding test piece. It is seen that the outer zone 2 did not loosen or peel off, however, it seems that the outer zone 2 of pure tantalum has yielded just at the fracture, which confirms that the outer zone 2 does not peel off and that the outer zone 2 has a higher ductility than the base body 1.

Figure 15:
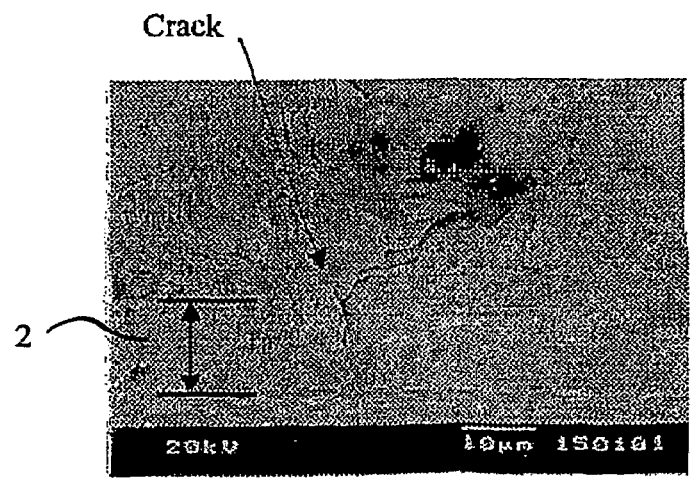
FIG. 15 is a view showing a crack in a base body.

FIG. 15 showing an enlargement of a base body 1 of stainless steel which has been surface modified by tantalum, is an example of a crack which seems to stop in the outer zone 2 of tantalum, which may be due to the fact that the outer zone 2 has a higher ductility than the base body 1, the concentration of stress at a crack tip being reduced, and that there are compressive stresses in the surface of the implant.

What is claimed is:

1. A process for electrochemical deposition of tantalum on an article in an inert, non-oxidizing atmosphere, or under vacuum, in a molten electrolyte containing tantalum ions, comprising the steps of:

immersing the article into the molten electrolyte heated to a working temperature, passing an electric current through the electrolyte to thereby deposit a tantalum coating on the article, using the process of tantalum deposition to at least in an initial phase deposit pure α-tantalum, wherein applying the electrical current in a first type of cycles in a nucleation phase, said first type of cycles comprising at least one cathodic period, followed by at least one anodic period, and a pause.

2. A process according to claim 1, whereby using a electrolyte based on a melt of fluorides and having a ratio of refractory metal to oxide content higher than 3:1.

3. A process according to claim 1, wherein during the nucleation phase the current is applied with pulses having a current density of between the limiting current density and the current density of β-tantalum deposition.

4. A process according to claim 1, wherein the current pulses have a duration longer than a charge/discharge of a double layer.

5. A process according to claim 1, wherein the duration of the pause is longer than the duration of the cathodic and anodic period of the cycle, preferably 2–8 times longer, in particular 4 times longer.

6. A process according to claim 1, wherein the current applied in the anodic period is higher than the current applied in the cathodic period.

7. A process according to claim 1, wherein the amount of electrical charge in the cathodic period is 1.2 to 8 times larger than the amount of charge in the anodic period, preferably 4 times larger.

8. An article, such as an implant, provided with a surface modification of tantalum by a process according to claim 1, wherein the surface modification is non-porous and at least comprises an interface layer of α-tantalum.

9. An article according to claim 8, wherein the surface modification has a thickness of at least 2 µm.

10. An article according to claim 8, wherein the surface modification has a thickness of about 2–14 µm, preferably more than 5 µm and less than 12 µm, and in particular 8–10 µm.

* * * * *